US007669596B2

(12) United States Patent
Alston

(10) Patent No.: US 7,669,596 B2
(45) Date of Patent: Mar. 2, 2010

(54) AEROSOLIZATION APPARATUS WITH ROTATING CAPSULE

(75) Inventor: William Alston, San Jose, CA (US)

(73) Assignee: Novartis Pharma AG, Basel (CH)

( * ) Notice: Subject to any disclaimer, the term of this patent is extended or adjusted under 35 U.S.C. 154(b) by 836 days.

(21) Appl. No.: 10/729,847

(22) Filed: Dec. 5, 2003

(65) Prior Publication Data
US 2005/0022813 A1 Feb. 3, 2005

Related U.S. Application Data

(60) Provisional application No. 60/437,225, filed on Dec. 31, 2002.

(51) Int. Cl.
*A61M 16/00* (2006.01)
(52) U.S. Cl. ............... 128/203.21; 128/203.15; 128/203.12
(58) Field of Classification Search ............ 128/203.21, 128/205.21, 200.24, 203.12, 20; 604/58–60; 424/456, 467
See application file for complete search history.

(56) References Cited

U.S. PATENT DOCUMENTS

| 3,991,761 | A | | 11/1976 | Cocozza |
| 4,069,819 | A | * | 1/1978 | Valentini et al. ....... 128/203.15 |
| 4,114,615 | A | | 9/1978 | Wetterlin |
| 4,247,066 | A | | 1/1981 | Frost et al. |
| 4,249,526 | A | * | 2/1981 | Dean et al. ............. 128/203.15 |
| 4,338,931 | A | | 7/1982 | Cavazza |
| 4,846,876 | A | | 7/1989 | Draber et al. |
| 4,995,385 | A | | 2/1991 | Valentini |
| 5,152,284 | A | | 10/1992 | Valentini |
| 5,458,135 | A | | 10/1995 | Patton et al. |
| 5,515,871 | A | | 5/1996 | Bittner et al. |
| 5,614,217 | A | * | 3/1997 | Chiprich et al. ............. 424/451 |
| 5,619,985 | A | | 4/1997 | Ohki et al. |
| 5,785,049 | A | | 7/1998 | Smith et al. |
| 5,921,236 | A | | 7/1999 | Ohki et al. |
| 5,922,675 | A | | 7/1999 | Baker et al. |
| 6,161,260 | A | | 12/2000 | Flewitt |
| 6,257,233 | B1 | | 7/2001 | Burr et al. |
| 6,273,086 | B1 | | 8/2001 | Ohki et al. |
| 6,357,490 | B1 | | 3/2002 | Johnston et al. |
| 6,705,313 | B2 | * | 3/2004 | Niccolai ................ 128/203.21 |

FOREIGN PATENT DOCUMENTS

| WO | 95/24183 | 9/1995 |
| WO | 96/32096 | 10/1996 |
| WO | 96/32149 | 10/1996 |
| WO | 99/16419 | 4/1999 |
| WO | 99/16422 | 4/1999 |
| WO | 00/07572 | 2/2000 |
| WO | 00/72904 | 12/2000 |

* cited by examiner

*Primary Examiner*—Justine R. Yu
(74) *Attorney, Agent, or Firm*—Michael J. Mazza

(57) ABSTRACT

An aerosolization apparatus comprises a body defining an inlet opening, an outlet opening, and an aerosolization chamber between the inlet opening and the outlet opening. The aerosolization chamber is adapted to receive an elongated receptacle, such as a capsule, containing a pharmaceutical formulation. The elongated receptacle rotates end-over-end about an axis substantially orthogonal to an axis passing through the outlet opening when air or gas flows through the body. In another version, the elongated receptacle rotates end-over-end about an axis substantially orthogonal to an inhalation direction.

20 Claims, 2 Drawing Sheets

AEROSOLIZATION APPARATUS WITH ROTATING CAPSULE

This application claims the benefit U.S. Provisional Patent Application Ser. No. 60/437,225 filed on Dec. 31, 2002, which is incorporated herein by reference in its entirety.

BACKGROUND

The need for effective therapeutic treatment of patients has resulted in the development of a variety of pharmaceutical formulation delivery techniques. One traditional technique involves the oral delivery of a pharmaceutical formulation in the form of a pill, capsule, elixir, or the like. However, oral delivery can in some cases be undesirable. For example, many pharmaceutical formulations may be degraded in the digestive tract before they can be effectively absorbed by the body. Inhalable drug delivery, where an aerosolized pharmaceutical formulation is orally or nasally inhaled by a patient to deliver the formulation to the patient's respiratory tract, has proven to be a particularly effective and/or desirable alternative. For example, in one inhalation technique, an aerosolized pharmaceutical formulation provides local therapeutic relief to a portion of the respiratory tract, such as the lungs, to treat diseases such as asthma, emphysema, and cystic fibrosis. In another inhalation technique, a pharmaceutical formulation is delivered deep within a patient's lungs where it may be absorbed into the blood stream. Many types of inhalation devices exist including devices that aerosolize a dry powder pharmaceutical formulation.

One type of inhalation device aerosolizes a pharmaceutical formulation that is stored in a capsule. For example, a dose or a portion of a dose of a dry powder pharmaceutical formulation may be stored in a capsule, and the capsule may be inserted into an aerosolization device which is capable of aerosolizing the pharmaceutical formulation. The aerosolization may be accomplished by releasing stored energy. For example, the aerosolization may be accomplished by utilizing energy supplied during the user's inhalation, such as the flow of inhaled air, to aerosolize the pharmaceutical formulation. After being inserted into the aerosolization device, the capsule is opened to expose the pharmaceutical formulation. The opening of the capsule may be performed, for example, by puncturing or tearing the capsule. When the capsule is properly opened and when aerosolization energy is supplied, the pharmaceutical formulation is aerosolized so that it may be inhaled by the user and a dose or portion of a dose of the aerosolized pharmaceutical formulation may be delivered to the user's respiratory tract.

The size and quality of the dose delivered to the user is dependent on the amount and condition of aerosolizable pharmaceutical formulation that exits the capsule. However, in conventional aerosolization devices, the amount and condition of the aerosolizable pharmaceutical formulation may vary from use to use and/or from user to user. For example, sometimes it is difficult to cause large amounts of the pharmaceutical formulation to exit the capsule when a user is unable to generate a high flow rate inhalation. In addition, it is sometimes difficult to cause large amounts of the pharmaceutical formulation to exit the capsule during very high flow rate inhalations due to compaction of the pharmaceutical formulation within the capsule. The inefficient release of pharmaceutical formulation can be costly and can result in the necessity for numerous operations of the device in order to achieve a desire dosage. In some circumstances, the pharmaceutical formulation exits the capsule in agglomerated form, the agglomerations being undesirably large for inhalation therapy.

Therefore, it is desirable to be able to aerosolize a pharmaceutical formulation in a consistent manner. It is further desirable to be able to aerosolize a pharmaceutical formulation in a manner that extracts an increased amount of the pharmaceutical formulation from a receptacle. It is also desirable to be able to aerosolize a pharmaceutical formulation in a more deagglomerated form.

SUMMARY

The present invention satisfies these needs. In one aspect of the invention, a receptacle rotates within an aerosolization chamber in an improved manner.

In another aspect of the invention, an aerosolization apparatus comprises a body defining an inlet opening, an outlet opening, and an aerosolization chamber between the inlet opening and the outlet opening, wherein the aerosolization chamber is adapted to receive an elongated receptacle containing a pharmaceutical formulation and wherein the elongated receptacle rotates end-over-end about an axis substantially orthogonal to an axis passing through the outlet opening when air or gas flows through the body.

In another aspect of the invention, an aerosolization apparatus is provided for delivering an aerosolized pharmaceutical formulation to a user's respiratory tract. The apparatus comprises a body defining an inlet opening, an outlet opening, and an aerosolization chamber between the inlet opening and the outlet opening, wherein the aerosolization chamber is adapted to receive an elongated receptacle containing a pharmaceutical formulation and wherein the elongated receptacle rotates end-over-end about an axis substantially orthogonal to an axis parallel to an inhalation direction when the user inhales to cause air or gas to pass through the body.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

DESCRIPTION

The present invention relates to an aerosolization apparatus. In particular, the invention relates to an aerosolization apparatus capable of aerosolizing a pharmaceutical formulation contained in a receptacle, such as a capsule. Although the process is illustrated in the context of aerosolizing a dry powder pharmaceutical formulation for inhalation, the present invention can be used in other processes and should not be limited to the examples provided herein.

Figure 1A:
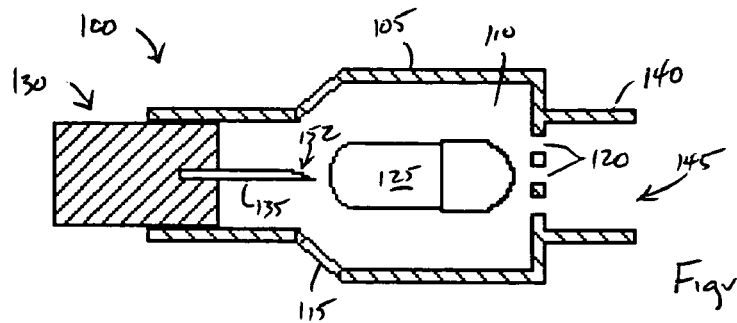
FIG. 1A is a schematic sectional side view of an aerosolization apparatus in an initial position.

An aerosolization apparatus 100 according to the present invention is shown schematically in FIG. 1A. The aerosolization apparatus 100 comprises a housing 105 defining a chamber 110 having one or more air inlets 115 and one or more air outlets 120. The chamber 110 is sized to receive a receptacle 125 which contains an aerosolizable pharmaceutical formulation. An opening mechanism 130 comprises an opening member 135 that is moveable within the chamber 110. Near or adjacent the outlet 120 is an end section 140 that may be sized and shaped to be received in a user's mouth or nose so that the user may inhale through an opening 145 in the end section 140 that is in communication with the outlet 120.

The aerosolization apparatus 100 utilizes air flowing through the chamber 110 to aerosolize the pharmaceutical formulation in the receptacle 125. For example, FIGS. 1A through 1E illustrate the operation of a version of an aerosolization apparatus 100 where air flowing through the inlet 115 is used to aerosolize the pharmaceutical formulation and the aerosolized pharmaceutical formulation flows through the outlet 120 so that it may be delivered to the user through the opening 145 in the end section 140. The aerosolization apparatus 100 is shown in its initial condition in FIG. 1A. The receptacle 125 is positioned within the chamber 110 and the pharmaceutical formulation is secured within the receptacle 125.

Figure 1B:
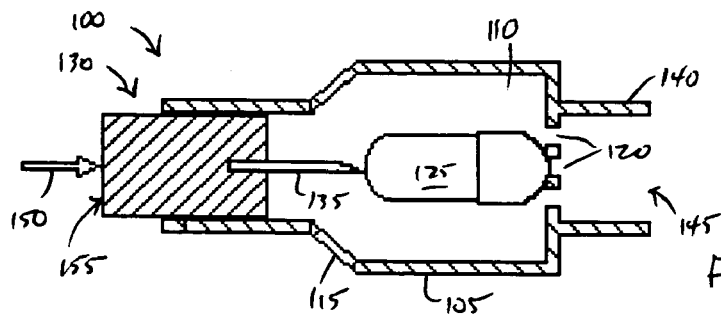
FIG. 1B is a schematic sectional side view of the aerosolization apparatus shown in FIG. 1A at the beginning a receptacle opening process.
Figure 1C:
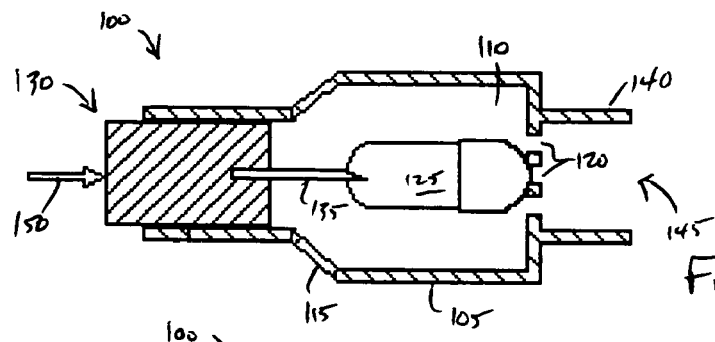
FIG. 1C is a schematic sectional side view of the aerosolization apparatus shown in FIG. 1A during the a receptacle opening process.
Figure 1D:
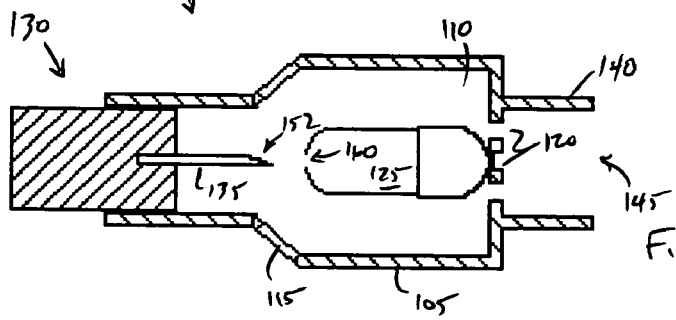
FIG. 1D is a schematic sectional side view of the aerosolization apparatus shown in FIG. 1A during the beginning of an aerosolization process.

To use the aerosolization apparatus 100, the pharmaceutical formulation in the receptacle 125 is exposed to allow it to be aerosolized. In the version of FIGS. 1A though 1E, the opening mechanism 130 is advanced within the chamber 110 by applying a force 150 to the opening mechanism 130. For example, a user may press against a surface 155 of the opening mechanism 130 to cause the opening mechanism 130 to slide within the housing 105 so that the opening member 135 contacts the receptacle 125 in the chamber 110, as shown in FIG. 1B. By continuing to apply the force 150, the opening member 135 is advanced to abut the wall of the receptacle 125 or to extend into the wall of the receptacle 125, as shown in FIG. 1C. The opening member may comprise one or more blunt or sharp tips 152 that contact the receptacle 125 in a manner that provides an opening into the receptacle 125. Examples of sharpened opening mechanisms are described in U.S. Pat. No. 4,069,819; in U.S. Pat. No. 4,995,385; and in U.S. Pat. No. 3,991,761, all of which are incorporated herein by reference in their entireties. The opening mechanism 130 is then retracted to the position shown in FIG. 1D, leaving an opening 160 through the wall of the receptacle 125 to expose the pharmaceutical formulation in the receptacle 125. Alternatively, a non-puncturing opening mechanism may be used, such as the mechanism described in U.S. Provisional Patent Application Ser. No. 60/437,254 filed on Dec. 31, 2002 and in the corresponding non-provisional application claiming the benefit thereof, both of which are incorporated herein by reference in their entireties.

Figure 1E:
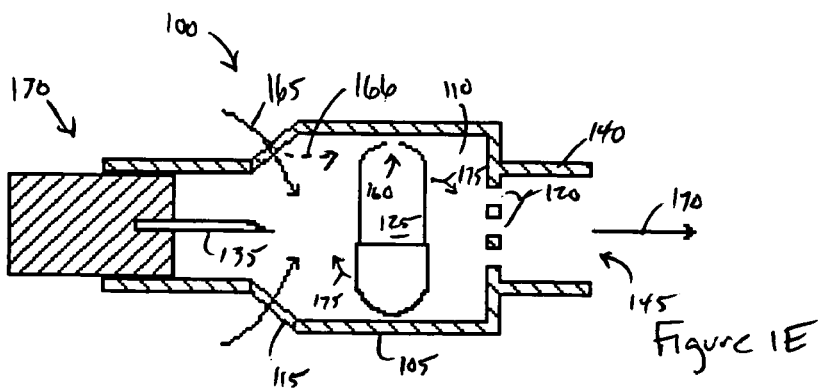
FIG. 1E is a schematic sectional side view of the aerosolization apparatus shown in FIG. 1A during the aerosolization process.

Air or other gas then flows through an inlet 115, as shown by arrows 165 in FIG. 1E. The flow of air causes the pharmaceutical formulation to be aerosolized. When the user inhales 170 through the end section 140 the aerosolized pharmaceutical formulation is delivered to the user's respiratory tract. In one version, the air flow 165 may be caused by the user's inhalation 170. In another version, compressed air or other gas may be ejected into the inlet 115 from a source of pressurized gas to cause the aerosolizing air flow 165.

As can be seen in FIG. 1E, the chamber 110 of the aerosolization apparatus 100 is shaped so that the receptacle 125 rotates within the chamber 110. The airflow is designed so that the receptacle 125 rotates in the direction of the arrows 175, that is in an end-over-end manner. The rotation is substantially about an axis that is substantially orthogonal to the inhalation direction 170 and/or to the direction through the outlet 120. In another version, the rotation is substantially about an axis that is substantially orthogonal to the inhalation direction 170 and/or to the direction through the outlet 120 and where a central longitudinal axis of the receptacle remains substantially within a vertical plane. By "substantially" it is meant within a deviation of 30 degrees.

The rotational motion of the receptacle shown in FIG. 1E allows for improved aerosolization. The rotation forces the pharmaceutical formulation in the receptacle 125 to be force outwardly through the opening 160. Accordingly, an increased amount of the pharmaceutical formulation is ejected from the receptacle 125 and is entrained in the airflow. In addition, the forces acting on the pharmaceutical formulation provide improved deagglomeration of the pharmaceutical formulation. In one version, the inlets 115 may be designed to encourage the end-over-end motion of the capsule. For example, an inlet may be formed so as to cause the air flow to take on the path shown 166 in section in FIG. 1E.

Figure 2A:
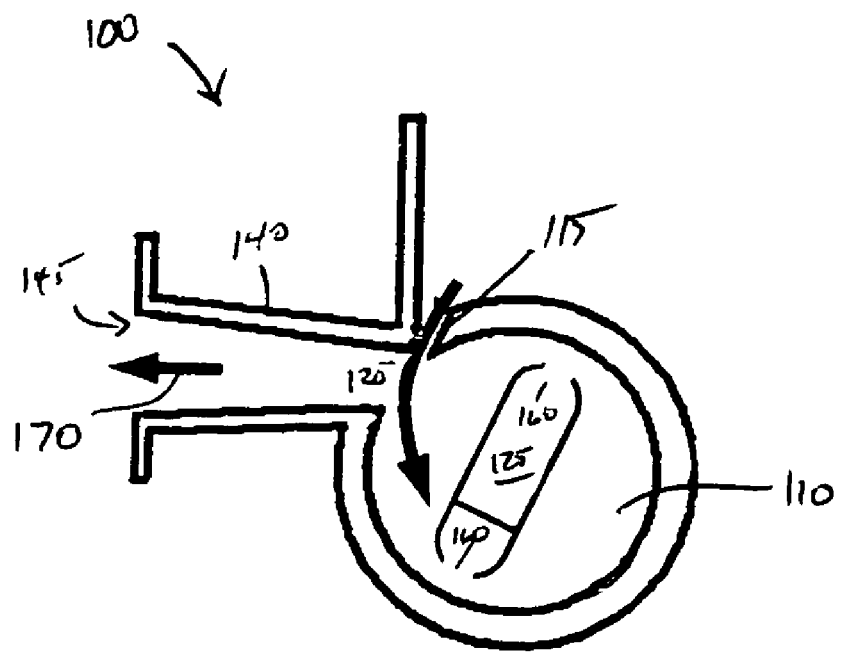
FIG. 2A is a schematic sectional side view of another version of an aerosolization apparatus of the invention.
Figure 2B:
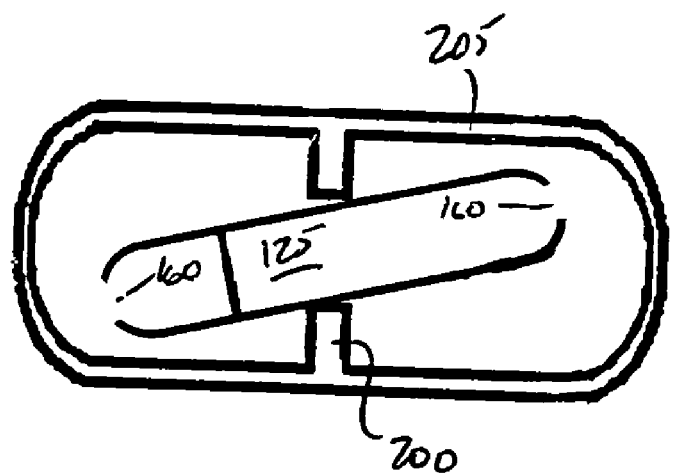
FIG. 2B is a schematic sectional top view of a portion of the version of an aerosolization apparatus shown in FIG. 2A.

A version of an aerosolization apparatus 100 having a chamber 110 accommodating a rotating receptacle 125 is shown in FIGS. 2A and 2B. FIG. 2A shows a cross-sectional side view of the aerosolization apparatus 100 in use. As can be seen, the aerosolization chamber 110 in this version is substantially circular. One or more inlets 115 are provided to create a circular airflow path that causes the receptacle 125 to rotate as discussed above. As can be seen in FIG. 2B, which is a top sectional view through the chamber 110, a constraining member 200 may be provided to constrain the receptacle 125 to the desired rotation. In one version, a sidewall 205 of the chamber may removable or may be hinged to the chamber 110 to allow access to the chamber 110 for insertion of the receptacle 125 thereinto. The one or more openings 160 into the receptacle 125 may be provided before insertion of the receptacle 125 into the chamber 110 or may be created within the chamber 110. For example, the openings 160 may be created by creating weakened portions on the receptacle 125 and then applying a force to the receptacle 125 to cause the weakened portions to open, as described in the aforementioned U.S. Provisional Patent Application Ser. No. 60/437,254 filed on Dec. 31, 2002 and in the aforementioned corresponding non-provisional application claiming the benefit thereof. Alternatively, a sharpened member may be provided in a portion of the chamber to create the opening in the receptacle as described in the aforementioned U.S. Pat. No. 3,991,761.

In another version, the aerosolization of the pharmaceutical formulation may be accomplished by pressurized gas flowing through the one or more inlets 115, as described for example in U.S. Pat. No. 5,458,135, U.S. Pat. No. 5,785,049, and U.S. Pat. No. 6,257,233, or propellant, as described in PCT Publication WO 00/72904 and U.S. Pat. No. 4,114,615. All of the above references being incorporated herein by reference in their entireties.

In one version, the receptacle 125 comprises a capsule type receptacle. The capsule may be of a suitable shape, size, and material to contain the pharmaceutical formulation and to provide the pharmaceutical formulation in a usable condition. For example, the capsule may comprise a wall which comprises a material that does not adversely react with the pharmaceutical formulation. In addition, the wall may comprise a material that allows the capsule to be opened to allow the pharmaceutical formulation to be aerosolized. In one version, the wall comprises one or more of gelatin, hydroxypropyl methylcellulose (HPMC), polyethyleneglycol-compounded HPMC, hydroxyproplycellulose, agar, or the like. Alternatively or additionally, the capsule wall may comprise a polymeric material, such as polyvinyl chloride (PVC). In one version, the capsule may comprise telescopically ajoined sections, as described for example in U.S. Pat. No. 4,247,066 which is incorporated herein by reference in its entirety. The interior of the capsule may be filled with a suitable amount of the pharmaceutical formulation, and the size of the capsule may be selected to adequately contain a desired amount of the pharmaceutical formulation. The sizes generally range from size 5 to size 000 with the outer diameters ranging from about 4.91 mm to 9.97 mm, the heights ranging from about 11.10 mm to about 26.14 mm, and the volumes ranging from about 0.13 ml to about 1.37 ml, respectively. Suitable capsules are available commercially from, for example, Shionogi Qualicaps Co. in Nara, Japan and Capsugel in Greenwood, S.C. After filling, a top portion may be placed over the bottom portion to form the a capsule shape and to contain the powder within the capsule, as described in U.S. Pat. No. 4,846,876, U.S. Pat. No. 6,357,490, and in the PCT application WO 00/07572 published on Feb. 17, 2000, all of which are incorporated herein by reference in their entireties.

In a preferred version, the invention provides a system and method for aerosolizing a pharmaceutical formulation and delivering the pharmaceutical formulation to the respiratory tract of the user, and in particular to the lungs of the user. The pharmaceutical formulation may comprise powdered medicaments, liquid solutions or suspensions, and the like, and may include an active agent.

The active agent described herein includes an agent, drug, compound, composition of matter or mixture thereof which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable active agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxidants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/Ella inhibitor, alpha-1 antitrypsin, phosphodiesterase (PDE) compounds, VLA-4 inhibitors, bisphosponates, respiratory syncytial virus antibody, cystic fibrosis transmembrane regulator (CFTR) gene, deoxyribonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicillinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition).

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

The pharmaceutical formulation may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts ranging from about 0.01% to about 95% percent by weight, preferably from about 0.5 to about 80%, and more preferably from about 1 to about 60% by weight. Preferably, such excipients will, in part, serve to further improve the features of the active agent composition, for example by providing more efficient and reproducible delivery of the active agent, improving the handling characteristics of powders, such as flowability and consistency, and/or facilitating manufacturing and filling of unit dosage forms. In particular, excipient materials can often function to further improve the physical and chemical stability of the active agent, minimize the residual moisture content and hinder moisture uptake, and to enhance particle size, degree of aggregation, particle surface properties, such as rugosity, ease of inhalation, and the targeting of particles to the lung. One or more excipients may also be provided to serve as bulking agents when it is desired to reduce the concentration of active agent in the formulation.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. Suitable excipients are those provided in WO 96/32096, which is incorporated herein by reference in its entirety. The excipient may have a glass transition temperature (Tg) above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility—enhancing peptide excipients include dimers, trimers, tetramers, and pentamers comprising one or more hydrophobic amino acid components such as those described above.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", 52$^{nd}$ ed., Medical Economics, Montvale, N.J. (1998), both of which are incorporated herein by reference in their entireties.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size. "Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

In one version, the powdered formulation for use in the present invention includes a dry powder having a particle size selected to permit penetration into the alveoli of the lungs, that is, preferably 10 μm mass median diameter (MMD), preferably less than 7.5 μm, and most preferably less than 5 μm, and usually being in the range of 0.1 μm to 5 μm in diameter. The delivered dose efficiency (DDE) of these powders may be greater than 30%, more preferably greater than 40%, more preferably greater than 50% and most preferably greater than 60% and the aerosol particle size distribution is about 1.0-5.0 μm mass median aerodynamic diameter (MMAD), usually 1.5-4.5 μm MMAD and preferably 1.5-4.0 μm MMAD. These dry powders have a moisture content below about 10% by weight, usually below about 5% by weight, and preferably below about 3% by weight. Such powders are described in WO 95/24183, WO 96/32149, WO 99/16419, and WO 99/16422, all of which are all incorporated herein by reference in their entireties.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the cooperating components may be reversed or provided in additional or fewer number. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. An aerosolization apparatus comprising:
   a body defining an inlet opening, an outlet opening, and an aerosolization chamber between the inlet opening and the outlet opening,
   wherein the aerosolization chamber is adapted to receive an elongated receptacle containing a pharmaceutical formulation and wherein the elongated receptacle rotates end-over-end about an axis substantially orthogonal to an axis passing through the outlet opening when air or gas flows through the body.

2. An aerosolization apparatus according to claim 1 further comprising an opening mechanism for creating an opening in the receptacle.

3. An aerosolization apparatus according to claim 2 wherein the opening mechanism comprises a sharpened tip moveable within the aerosolization chamber.

4. An aerosolization apparatus according to claim 1 further comprising the receptacle.

5. An aerosolization apparatus according to claim 4 wherein the receptacle comprises a capsule.

6. An aerosolization apparatus according to claim 5 wherein the capsule comprises a wall comprising one or more of gelatin, hydroxypropyl methylcellulose, polyethyleneglycol-compound hydroxypropyl methylcellulose, hydroxyproplycellulose, and agar.

7. An aerosolization apparatus according to claim 5 wherein the receptacle contains a powder pharmaceutical formulation.

8. An aerosolization apparatus according to claim 7 wherein the powder pharmaceutical formulation comprises particles having a mass median diameter less than 10 μm.

9. An aerosolization apparatus according to claim 7 wherein the powder pharmaceutical formulation has a moisture content below 5% by weight.

10. An aerosolization apparatus for delivering an aerosolized pharmaceutical formulation to a user's respiratory tract, the apparatus comprising:
    a body defining an inlet opening, an outlet opening, and an aerosolization chamber between the inlet opening and the outlet opening,
    wherein the aerosolization chamber is adapted to receive an elongated receptacle containing a pharmaceutical formulation and wherein the elongated receptacle rotates end-over-end about an axis substantially orthogonal to an axis parallel to an inhalation direction when the user inhales to cause air or gas to pass through the body.

11. An aerosolization apparatus according to claim 10 wherein the inhalation direction is a direction coincident with an axis passing through a mouthpiece of the apparatus.

12. An aerosolization apparatus according to claim 10 further comprising an opening mechanism for creating an opening in the receptacle.

13. An aerosolization apparatus according to claim 12 wherein the opening mechanism comprises a sharpened tip moveable within the aerosolization chamber.

14. An aerosolization apparatus according to claim 10 further comprising the receptacle.

15. An aerosolization apparatus according to claim 14 wherein the receptacle comprises a capsule.

16. An aerosolization apparatus according to claim 15 wherein the capsule comprises a wall comprising one or more of gelatin, hydroxypropyl methylcellulose, polyethyleneglycol-compounded hydroxypropyl methylcellulose, hydroxyproplycellulose, and agar.

17. An aerosolization apparatus according to claim 15 wherein the receptacle contains a powder pharmaceutical formulation.

18. An aerosolization apparatus according to claim 17 wherein the powder pharmaceutical formulation comprises particles having a mass median diameter less than 10 μm.

19. An aerosolization apparatus according to claim 17 wherein the powder pharmaceutical formulation has a moisture content below 5% by weight.

20. An aerosolization apparatus according to claim 10 wherein the inlet opening is shaped to cause a swirling air or gas flow through the chamber.

* * * * *